Figure 1:
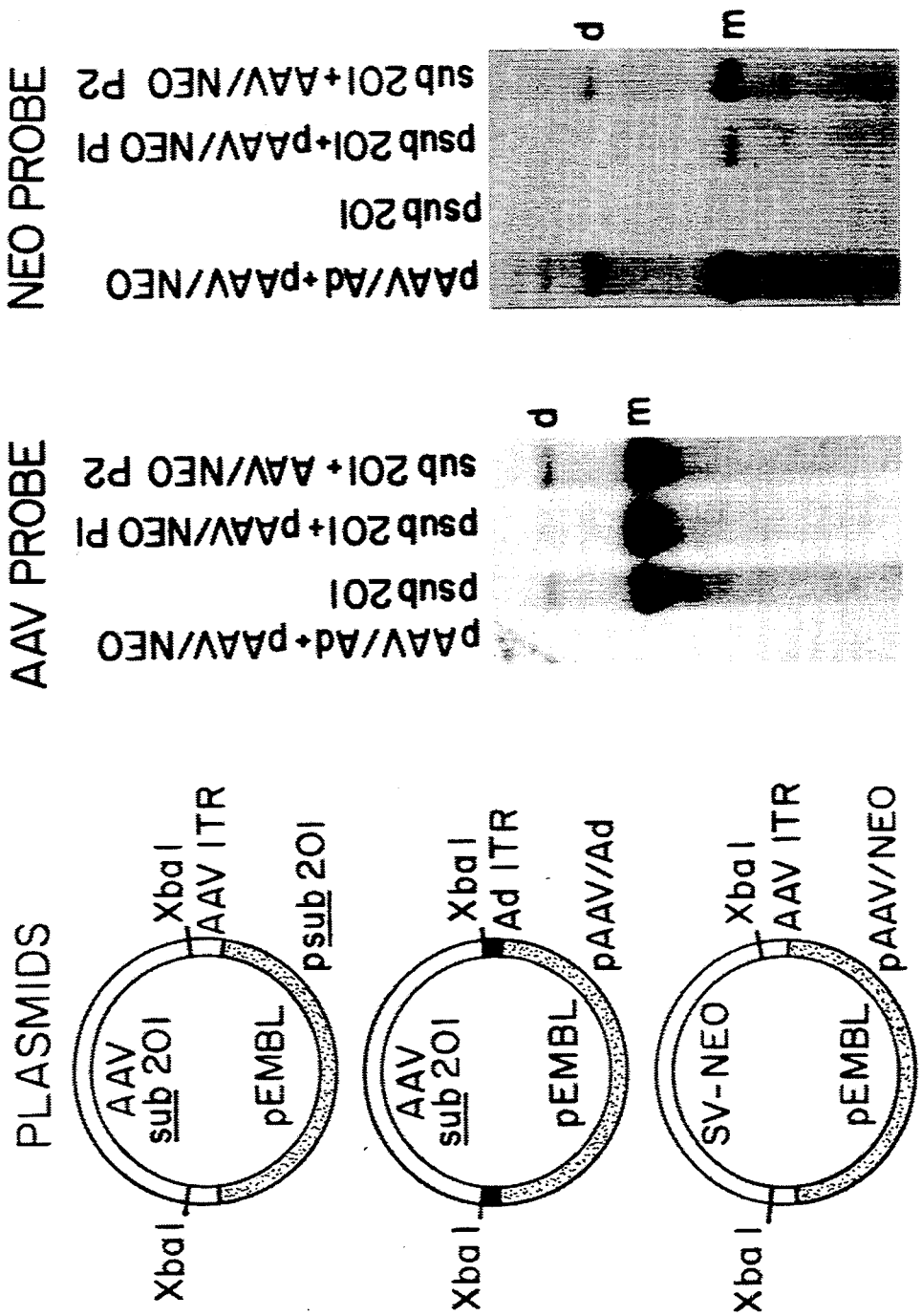

United States Patent [19]
Shenk et al.

[11] Patent Number: 5,436,146
[45] Date of Patent: Jul. 25, 1995

[54] HELPER-FREE STOCKS OF RECOMBINANT ADENO-ASSOCIATED VIRUS VECTORS

[75] Inventors: Thomas E. Shenk, Princeton, N.J.; Richard J. Samulski, Pittsburgh, Pa.; Long-Sheng Chang, Linden, N.J.

[73] Assignee: The Trustees of Princeton University, Princeton, N.J.

[21] Appl. No.: 7,399

[22] Filed: Jan. 21, 1993

Related U.S. Application Data

[63] Continuation of Ser. No. 404,149, Sep. 7, 1989, abandoned.

[51] Int. Cl.$^6$ ............ C12N 15/00; C12N 5/10; C12N 7/01; C12N 15/35
[52] U.S. Cl. .................. 435/172.3; 435/240.2; 435/235.1; 435/320.1; 435/91.4; 536/23.72
[58] Field of Search .............. 435/235.1, 320.1, 172.3, 435/240.2, 91.4; 935/32, 57, 70, 71; 536/23.72; 424/199.1, 93.2

[56] References Cited

U.S. PATENT DOCUMENTS 4,797,368 1/1989 Carter et al. ................. 435/320.1

OTHER PUBLICATIONS

Labow, M. A. et al. 1988, J. Virol. vol. 62 pp. 1705–1712.
DeLaMaza, L. M. et al. 1980 *J. Biol. Chem.* vol. 255 pp. 3194–3203.
Lebkowski, J. et al. 1988. *Molecular and Cellular Biology*, vol. 8 pp. 3988–3996.
Samulski, R. J. et al. 1987. *Journal of Virology*, vol. 61, pp. 3096–3101.
McLaughlin, S. K. et al. 1988. *Journal of Virology*, vol. 62, pp. 1963–1973.
Miller, A. D. et al. *Somatic Cell and Molecular Genetics*, vol. 12, pp. 175–183.
Bosselman, R. A. et al. 1987. *Molecular and Cellular Biology*, vol. 7, pp. 1979–1806.
Laface et al., 1988, Virology 162:483–486.
Ohi et al., 1988, J. Cell Biol. 107:304A.
Wondisford et al., 1988, Mol. Endocrinol. 2:32–39.
Hermonat and Muzyczka, 1984, Proc. Natl. Acad. Sci. U.S.A. 81:6466–6470.
Senapathy et al., 1984, J. Mol. Biol. 179:1–20.
Tratschin et al., 1984, Mol. Cell. Biol. 4:2072–2081.
Laughlin et al., 1983, Gene 23:65–73.
Samulski et al., 1983, Cell 33:135–143.
Samulski et al., 1982, Proc. Natl. Acad. Sci. U.S.A. 79:2077–2081.

*Primary Examiner*—Mary E. Mosher
*Attorney, Agent, or Firm*—Pennie & Edmonds

[57] ABSTRACT

The present invention relates to a method for producing helper-free stocks of recombinant adeno-associated virus (rAAV) which can be used to efficiently and stably transduce foreign genes into host cells or organisms. The method comprises the cotransfection of eukaryotic cells with rAAV and with helper AAV DNA in the presence of helper virus (e.g. adenovirus or herpesvirus) such that the helper AAV DNA is not associated with virion formation. The crux of the invention lies in the inability of the helper AAV DNA to recombine with rAAV vector, thereby preventing the generation of wild-type virus. In a specific embodiment of the invention, the vector comprises a recombinant AAV genome containing only the terminal regions of the AAV chromosome bracketing a non-viral gene, and the helper AAV DNA comprises a recombinant AAV genome containing that part of the AAV genome which is not present in the vector, and in which the AAV terminal regions are replaced by adenovirus sequences. In a further embodiment of the invention, cell lines are created which incorporate helper AAV DNA which can directly produce substantially pure recombinant AAV virus. The pure stocks of recombinant AAV produced according to the invention provide an AAV viral expression vector system with increased yield of recombinant virus, improved efficiency, higher definition, and greater safety than presently used systems.

47 Claims, 5 Drawing Sheets

FIG.2

HELPER-FREE STOCKS OF RECOMBINANT ADENO-ASSOCIATED VIRUS VECTORS

This is a continuation of application Ser. No. 07/404,149, filed Sep. 7, 1989, now abandoned.

TABLE OF CONTENTS

1. Field of Invention
2. Background of the Invention
   2.1. Viral Vectors
   2.2. Adeno-Associated Virus
   2.3. Recombinant Adeno-Associated Virus
3. Summary of the Invention
   3.1. Definitions
4. Description of the Figures
5. Detailed Description of the Invention
   5.1. The Vector/Helper AAV Virus Relationship
   5.2. Recombinant Adeno-Associated Virus Vectors
   5.3. Helper Adeno-Associated DNA
   5.4. Production of Helper-Free Recombinant AAV Stocks
   5.5. Utility of Helper-Free Recombinant AAV Stocks
6. Example: Helper-Free Stocks of Recombinant Adeno-Associated Viruses (AAV): Normal Integration Does Not Require Viral Gene Expression
   6.1. Materials and Methods
      6.1.1. Plasmids and Viruses
      6.1.2. Cell Cultures
      6.1.3. DNA Replication and Excision Assays
      6.1.4. DNA Blot Analysis
      6.1.5. Protein Analysis
   6.2. Results
      6.2.1. Recombinant AAV Stocks That Contain No Detectable Helper AAV
      6.2.2. Normal Integration of Recombinant DNAs in the Absence of AAV Gene Expression
   6.3. Discussion
      6.3.1. Helper Virus-Free Stocks of Recombinant Viruses
      6.3.2. Normal Integration Without AAV Gene Expression
      6.3.3. High Efficiency Transduction With Recombinant Viruses
7. Deposit of Microorganisms

1. FIELD OF THE INVENTION

The present invention relates to a method for producing substantially pure stocks of recombinant adeno-associated virus (AAV), free of the adeno-associated helper virus found associated with previously available recombinant AAV. According to the invention, the substantially pure stocks of recombinant AAV may be used to introduce exogenous genetic sequences into cells, cell lines, or organisms; in the absence of the adeno-associated helper virus, the recombinant AAV will remain stably integrated into cellular DNA. In another embodiment of the invention cells containing integrated recombinant AAV may be exposed to helper viruses, resulting in excision, replication, and amplification of integrated sequences, thereby providing a means for achieving increased expression of gene product. The present invention also provides for novel recombinant AAV vectors and adeno-associated helper viruses.

2. BACKGROUND OF THE INVENTION

2.1. VIRAL VECTORS

Viral vectors permit the expression of exogenous genes in eukaryotic cells, and thereby enable the production of proteins which require postranslational modifications unique to animal cells. Viral expression vectors (reviewed in Rigby, 1983, J. Gen. Virol. 64: 255-266) have been developed using DNA viruses, such as papovaviruses (i.e. SV40), adenoviruses, herpes viruses, and poxviruses (i.e. vaccinia virus, Mackett et al., 1982, Proc. Natl. Acad. Sci. U.S.A. 79:7415-7419; Panicoli et al., 1982, Proc. Natl. Acad. Sci. U.S.A. 79:4927-4931) and RNA viruses, such as retroviruses.

In disclosing the construction and applications of a murine retrovirus shuttle vector, Cepko et al. (1984, Cell 37:1053-1062) cites several properties which may be desirable in a mammalian gene transfer system, including the ability of the vector to be introduced into a wide range of hosts and the recoverability of transferred sequences as molecular clones (i.e. a vector which can "shuttle" between animal and bacterial cells; see DiMaio et al., 1982, Proc. Natl. Acad. Sci. U.S.A. 79:4030-4034). As efficient shuttle vectors, retroviruses have become a popular vehicle for transferring genes into eukaryotic cells. Retrovirus packaging cell lines (Mann et al., 1983, Cell 33:153-159; Watanabe and Temin, 1983, Mol. Cell. Biol. 3:2241-2249; Cohn and Mulligan, 1984, Proc. Natl. Acad. Sci. U.S.A. 81:6349-6353; Sorge et al., 1984, Mol. Cell. Biol. 4:1730-1737) allow production of replication-defective retrovirus vectors in the absence of helper virus; the defective retroviral vectors are able to infect and integrate into cells but cannot replicate. The ability to produce helper-free stocks of defective retroviruses using packaging cell lines protects against spread of the recombinant virus, and avoids possible dissemination of recombinant virus-induced disease. However, some retrovirus packaging lines have been shown to produce only low titers of retroviral vectors, or produce high levels of helper virus; furthermore, some retroviruses exhibit limited host ranges (Miller and Baltimore, 1986, Mol. Cell. Biol. 6:2895-2902). The recognition of human retroviruses over the past decade as the etiologic agent of Acquired Immunodeficiency Syndrome (AIDS) and some cases of T-cell and hairy cell leukemia, and the numerous examples of oncogenic animal retroviruses, have created an awareness of health risks potentially associated with the use of retrovirus vectors, particularly relevant to future prospects in human gene therapy. Many of the alternative viral vectors currently available either do not integrate into host cells at high frequency, are not easily rescuable from the integrated state, are limited in their host range, or include other viral genes, thereby creating a need for the development of a safe and efficient viral vector system.

2.2. ADENO-ASSOCIATED VIRUS

Adeno-associated virus (AAV) is a defective member of the parvovirus family. The AAV genome is encapsidated as a single-stranded DNA molecule of plus or minus polarity (Berns and Rose, 1970, J. Virol. 5:693-699; Blacklow et al., 1967, J. Exp. Med. 115:755-763). Strands of both polarities are packaged, but in separate virus particles (Berns and Adler, 1972, Virology 9:394-396) and both strands are infectious (Samulski et al., 1987, J. Virol. 61:3096-3101).

The single-stranded DNA genome of the human adeno-associated virus type 2 (AAV2) is 4681 base pairs in length and is flanked by inverted terminal repeated sequences of 145 base pairs each (Lusby et al., 1982, J. Virol. 41:518–526). The first 125 nucleotides form a palindromic sequence that can fold back on itself to form a "T"-shaped hairpin structure and can exist in either of two orientations (flip or flop), leading to the suggestion (Berns and Hauswirth, 1979, Adv. Virus Res. 25:407–449) that AAV may replicate according to a model first proposed by Cavalier-Smith for linear-chromosomal DNA (1974, Nature 250:467–470) in which the terminal hairpin of AAV is used as a primer for the initiation of DNA replication. The AAV sequences that are required in cis for packaging, integration/rescue, and replication of viral DNA appear to be located within a 284 base pair (bp) sequence that includes the terminal repeated sequence (McLaughlin et al., 1988, J. Virol. 62:1963–1973).

At least three regions which, when mutated, give rise to phenotypically distinct viruses have been identified in the AAV genome (Hermonat et al., 1984, J. Virol. 51:329–339). The rep region codes for at least four proteins (Mendelson et al., 1986, J. Virol. 60:823–832) that are required for DNA replication and for rescue from the recombinant plasmid. The cap and lip regions appear to encode for AAV capsid proteins; mutants containing lesions within these regions are capable of DNA replication (Hermonat et al., 1984, J. Virol. 51:329–339). AAV contains three transcriptional promoters (Carter et al., 1983, in "The Parvoviruses" K. Berns ed., Plenum Publishing Corp., N.Y. pp. 153–207; Green and Roeder, 1980, Cell 22:231–242; Laughlin et al., 1979, Proc. Natl. Acad. Sci. U.S.A. 76:5567–5571; Lusby and Berns, 1982, J. Virol. 41:518–526; Marcus et al., 1981, Eur. J. Biochem. 121:147–154). The viral DNA sequence displays two major open reading frames, one in the left half and the other in the right half of the conventional AAV map (Srivastava et al., 1985, J. Virol. 45:555–564).

AAV-2 can be propagated as a lytic virus or maintained as a provirus, integrated into host cell DNA (Cukor et al., 1984, in "The Parvoviruses," Berns ed., Plenum Publishing Corp., N.Y. pp. 33–66). Although under certain conditions AAV can replicate in the absence of helper virus (Yakobson et al., 1987, J. Virol. 61:972–981), efficient replication requires coinfection with either adenovirus (Atchinson et al., 1965, Science 194:754–756; Hoggan, 1965, Fed. Proc. Am. Soc. Exp. Biol. 24:248; Parks et al., 1967, J. Virol. 1:171–180); herpes simplex virus (Buller et al., 1981, J. Virol. 40:241–247) or cytomegalovirus, Epstein-Barr virus, or vaccinia virus. Hence the classification of AAV as a "defective" virus.

When no helper virus is available, AAV can persist in the host cell genomic DNA as an integrated provirus (Berns et al., 1975, Virology 68:556–560; Cheung et al., 1980, J. Virol. 33:739–748). Virus integration appears to have no apparent effect on cell growth or morphology (Handa et al., 1977, Virology 82:84–92; Hoggan et al, 1972, in "Proceedings of the Fourth Lepetit Colloquium," North Holland Publishing Co., Amsterdam pp. 243–249). Studies of the physical structure of integrated AAV genomes (Cheung et al., 1980, supra; Berns et al., 1982, in "Virus Persistence" Mahy et al., eds., Cambridge University Press, N.Y. pp. 249–265) suggest that viral insertion occurs at random positions in the host chromosome but at a unique position with respect to AAV DNA, occurring within the terminal repeated sequence. Integrated AAV genomes have been found to be essentially stable, persisting in tissue culture for greater than 100 passages (Cheung et al., 1980 supra).

Although AAV is believed to be a human virus, its host range for lytic growth is unusually broad. Virtually every mammalian cell line (including a variety of human, simian, and rodent cell lines) evaluated could be productively infected with AAV, provided that an appropriate helper virus was used (Cukor et al., 1984, in "The Parvoviruses" Berns ed Plenum Publishing Corp , N.Y., pp 33–66).

No disease has been associated with AAV in either human or animal populations (Ostrove et al., 1987, Virology 113:521–533) despite widespread exposure and apparent infection. Anti-AAV antibodies have been frequently found in humans and monkeys. It is estimated that about 70 to 80 percent of children acquire antibodies to AAV types 1, 2, and 3 within the first decade; more than 50 percent of adults have been found to maintain detectable anti-AAV antibodies. AAV has been isolated from fecal, ocular, and respiratory specimens during acute adenovirus infections, but not during other illnesses (Dulbecco and Ginsberg, 1980, in "Virology" reprinted from Davis, Dulbecco, Eisen and Ginsberg's "Microbiology" Third Edition, Harper and Row Publishers, Hagerstown, p. 1059).

2.3. RECOMBINANT ADENO-ASSOCIATED VIRUS

Samulski et al., (1982, Proc. Natl. Acad. Sci. U.S.A. 79:2077–2081) cloned intact duplex AAV DNA into the bacterial plasmid pBR322 and found that the AAV genome could be rescued from the recombinant plasmid by transfection of the plasmid DNA into human cells with adenovirus 5 as helper. The efficiency of rescue from the plasmid was sufficiently high to produce yields of AAV DNA comparable to those observed after transfection with equal amounts of purified virion DNA.

The AAV sequences in the recombinant plasmid could be modified, and then "shuttled" into eukaryotic cells by transfection. In the presence of helper adenovirus, the AAV genome was found to be rescued free of any plasmid DNA sequences and replicated to produce infectious AAV particles (Samulski et al., 1982, Proc. Natl. Acad. Sci. 79:2077–2081; Laughlin et al., 1983, Gene 23:65–73; Samulski et al., 1983, Cell 33:135–143; Senapathy et al., 1984, J. Mol. Biol. 179:1–20).

The AAV vector system has been used to express a variety of genes in eukaryotic cells. Hermonat and Muzyczka (1984, Proc. Natl. Acad. Sci. U.S.A. 81:6466–6470) produced a recombinant AAV (rAAV) viral stock in which the neomycin resistance gene (neo) was substituted for AAV capsid gene and observed rAAV transduction of neomycin resistance into murine and human cell lines. Tratschen et al. (1984), Mol. Cell. Biol. 4:2072–2081) created a rAAV which was found to express the chloramphenicol acetyltransferase (CAT) gene in human cells. Lafare et al. (1988, Virology 162:483–486) observed gene transfer into hematopoietic progenitor cells using an AAV vector. Ohi et al. (1988, J. Cell. Biol. 107:304A) constructed a recombinant AAV genome containing human $\beta$-globin cDNA. Wondisford et al. (1988, Mol. Endocrinol. 2:32–39) cotransfected cells with two different recombinant AAV vectors, each encoding a subunit of human thyrotropin, and observed expression of biologically active thyrotropin.

Several AAV vector systems have been designed. Samulski et al. (1987, J. Virol. 61:3096–3101) constructed an infectious adeno-associated viral genome that contains two XbaI cleavage sites flanking the viral coding domain; these restriction enzyme cleavage sites were created to allow nonviral sequences to be inserted between the cis-acting terminal repeats of AAV.

U.S. Pat. No. 4,797,368, Carter and Tratschen, filed May 15, 1985, issued Jan. 10, 1989 relates to AAV vectors contained in a plasmid, capable of being packaged into AAV particles, and functioning as a vector for stable maintenance or expression of a gene or a DNA sequence in eukaryotic cells when under control of an AAV transcription promoter.

A problem encountered in all AAV systems prior to the present invention has been the inability to produce recombinant virus stocks free of helper AAV virus. The presence of helper AAV virus can potentially result in continued spread of recombinant AAV, could detract from the efficiency of rAAV production and the transduction of foreign genes, and could interfere with efficient expression of the foreign genes. Further, recombinant virus stocks produced using prior AAV helper systems did not produce a linear increase in the number of cells containing stably integrated recombinant virus DNA as the multiplicity of infection increased. This presumably resulted, at least in part, from inhibitory effects of AAV gene products expressed by helper AAV virus.

Various methods have been used in attempts to decrease the percentage of contaminating helper virus. Hormonat and Muzyczka (1984, supra) inserted bacteriophage λ sequences into a nonessential region of rAAV which resulted in a DNA length too large to package into virions; a variable number of virions containing wild-type AAV continued to contaminate rAAV stocks. Lebkowski et al. (1988, Mol. Cell. Biol. 3:3988–3996) report a method for producing recombinant AAV stocks with minimal contamination by wild-type virus, in which deletion mutant AAV are used to complement recombinant AAV viral functions. According to the method of Lebkowski et al., two independent recombinant events were required to produce wild-type contaminants. However, given the large number of viral particles produced during productive infection, a significant number of wild-type virus were generated which contaminated the recombinant stock. U.S. Pat. No. 4,797,368 uses various methods including using rep(-) (replication deficient) helper virus, to reduce the level of contaminating wild-type AAV, but acknowledge that "it is not as yet possible to completely avoid generation of wild-type recombinants."

3. SUMMARY OF THE INVENTION

The present invention relates to a method for producing substantially helper-free stocks of recombinant adeno-associated virus (rAAV) which can be used to efficiently and stably transduce foreign genes into host cells or organisms. The method comprises the cotransfection of eukaryotic cells with rAAV and with helper AAV DNA in the presence of helper virus (e.g. adenovirus or herpesvirus) such that the helper AAV DNA is not associated with virion formation. The crux of the invention lies in the inability of the helper AAV DNA to recombine with rAAV, thereby preventing the generation of wild-type virus.

In a specific embodiment of the invention, the vector comprises a recombinant AAV genome containing only the terminal regions of the AAV chromosome bracketing a non-viral gene, and the helper AAV DNA comprises a recombinant AAV genome containing that part of the AAV genome which is not present in the vector, and in which the AAV terminal regions are replaced by adenovirus terminal sequences. The substantially pure stocks of recombinant AAV produced according to the invention provide an AAV viral expression vector system with-efficient yield of helper-free recombinant virus. These stocks are able to introduce a foreign gene into a recipient cell at higher efficiency than has been obtained previously using stocks that contain helper AAV virus.

In a further embodiment of the invention, the helper AAV virus DNA may be incorporated into a cell line, such that rAAV constructs may be grown directly, without a need for separate helper AAV DNA.

3.1 DEFINITIONS helper virus: a virus such as adenovirus, herpesvirus, cytomegalovirus, Epstein-Barr virus, or vaccinia virus, which when coinfected with AAV results in productive AAV infection of an appropriate eukaryotic cell.

helper AAV DNA: AAV DNA sequences used to provide AAV functions to a recombinant AAV virus which lacks the functions needed for replication and/or encapsulation of DNA into virus particles. Helper AAV DNA cannot by itself generate infectious virions and may be incorporated within a plasmid, bacteriophage or chromosomal DNA.

helper-free virus stocks of recombinant AAV: stocks of recombinant AAV virions which contain no measurable quantities of wild-type AAV or undesirable recombinant AAV.

rAAV vector: recombinant AAV which contains foreign DNA sequences and can be produced as infectious virions.

a lower case "p" placed in conjunction with the name of a virus, e.g., sub201, to form psub201, denotes the virus inserted into a plasmid.

4. DESCRIPTION OF THE FIGURES

FIG. 1. Diagrams of AAV-containing plasmid DNAs and analysis of AAV rescue from transfected plasmid DNAs. (A) Structure of psub201, pAAV/Ad and pAAV/neo. pEMBL8(+) sequences are shaded, AAV inverted terminal repeats (ITR) are open and adenovirus (Ad) ITRs are solid. XbaI cleavage sites separating ITR sequences from AAV coding or neomycin resistance (SV-neo) sequences are indicated. (B and C) Blot analysis of replicating DNA that contains AAV-specific or SV-neo sequences. Low-molecular-weight DNA was prepared at 40 hr after HeLa cells were transfected with indicated plasmid DNAs, or infected with sub201 plus AAV/neo virus, and simultaneously infected with adenovirus at a multiplicity of 10 pfu/cell. After electrophoresis, DNA fragments were transferred to nitrocellulose and probed with either the XbaI fragment from psub201 containing only AAV-specific coding sequences (AAV probe, panel B) or the XbaI fragment from pAAV/neo containing only SV-neo coding sequences (neo probe, panel C). AAV-specific monomer (m) and dimer (d) DNAs are labeled.

Figure 2:
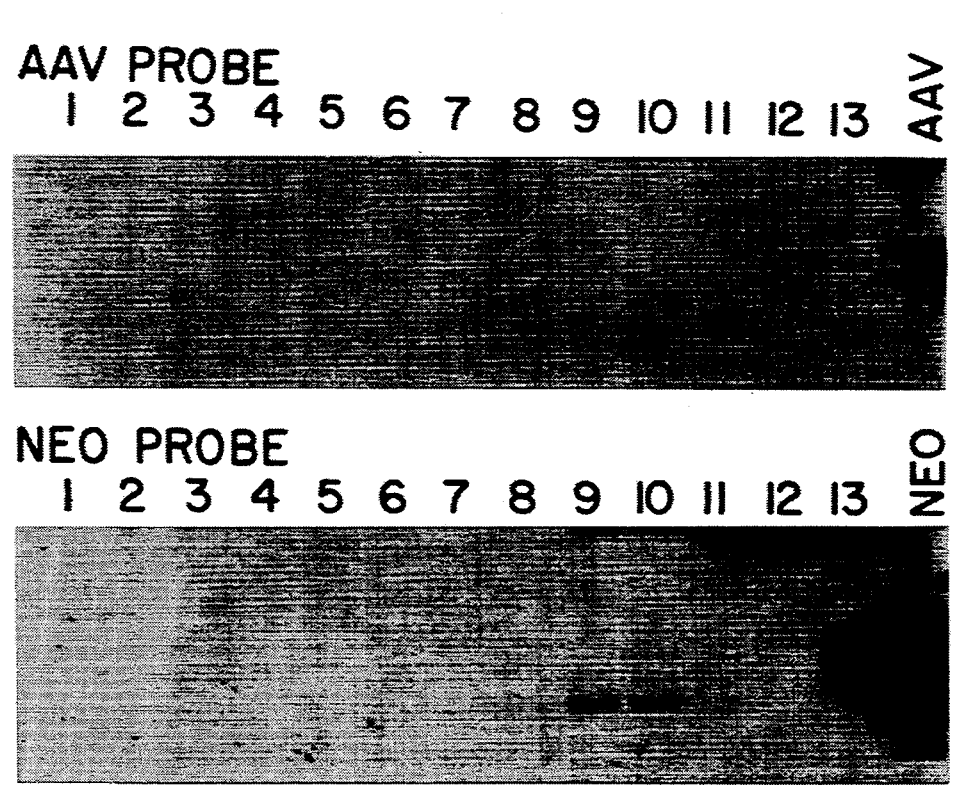

FIG. 2. Analysis of DNA sequences present in recombinant stocks of AAV/neo virus. HeLa cells were transfected with pAAV/neo plus pAAV/Ad DNA as helper in the presence of adenovirus. 40 hr later, lysates were prepared, adenovirus was inactivated by heating at 56° C. for 30 min, and AAV virions were subjected to equilibrium density centrifugation. Gradients were fractionated, DNA was extracted from each fraction, and subjected to DNA blot analysis using, first, an AAV-specific coding sequence as probe DNA (top panel), and, then after stripping the nitrocellulose filter, a neo-specific sequence as probe (bottom panel). The two probe DNAs were labeled to nearly identical specific activities. The top of each gradient is at the right, and the right hand most lane contains marker sequences homologous to the probe DNA (considerably more neo than AAV marker was added) to provide positive controls.

Figure 3:
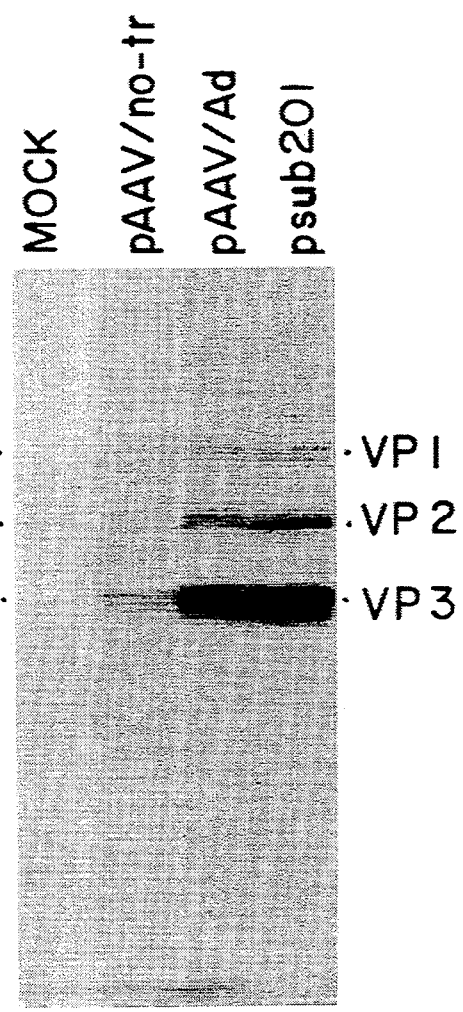

FIG. 3. Electrophoretic analysis of AAV capsid proteins synthesized at 40 hr after transfection of HeLa cells with pAAV/no-tr, pAAV/Ad or psub201. Cells were simultaneously transfected with indicated plasmid DNAs and infected with adenovirus at a multiplicity of 10 pfu/cell. At 40 hr after transfection/infection cells were labeled for 1 hr with [$^{35}$S]methionine, extracts were prepared, subjected to immunoprecipitation with a monoclonal antibody prepared against AAV capsids, and analyzed by electrophoresis in an SDS-containing polyacrylamide gel. Bands corresponding to the three capsid proteins VP1, VP2 and VP3 are indicated.

FIG. 4. Analysis of AAV-specific DNAs rescued from G418-resistant cell lines produced by infection with AAV/neo virus. G418-resistant cell lines containing rescuable AAV/neo genomes were infected with either adenovirus alone (Ad) or adenovirus plus sub201 (Ad+AAV). Low molecular weight DNA was prepared at 40 hr after infection and analyzed by DNA blot analysis using as probe DNA either the XbaI fragment from psub201 containing only AAV-specific coding sequences (AAV probe, panel A) or the equivalent fragment from pAAV/neo containing only SV-neo sequences (neo probe, panel B). Monomer (m) and dimer (d) AAV DNA molecules are labeled.

FIG. 5. DNA blot analysis of AAV/neo-specific sequences integrated in G418-resistant cell lines. (A) Diagram of BamH1 (B) and EcoRI (E) cleavage sites within AAV/neo DNA, and the affect of head-to-tail dimerization on predicted cleavage products. (B and C) Blot analysis of DNA prepared from rescuable and non-rescuable cell lines. High molecular weight DNA was cut with indicated enzymes and subjected to blot analysis using the XbaI fragment from pAAV/neo containing only SV-neo sequences as probe DNA. The positions of monomer (m) and dimer (d) AAV/neo DNAs are indicated.

5. DETAILED DESCRIPTION OF THE INVENTION

The present invention relates to a method for producing substantially helper-free stocks of recombinant AAV and is directed toward producing a viral expression vector system with improved efficiency, applicability, definition, and safety relative to viral vector systems currently utilized. The method of the invention utilizes a two component system comprised of functionally, but not structurally, related rAAV genomes, one of which contains cis-acting sequences needed for DNA replication and packaging and a segment of foreign DNA (the vector), but lacks DNA sequences encoding trans-acting products necessary for viral replication; and the other (the helper AAV DNA) which provides those trans-acting viral functions not encoded by the vector, but which cannot, itself, be replicated or incorporated into virions at detectable levels. Importantly, the vector and the helper DNA should be sufficiently nonhomologous so as to preclude homologous recombination events which could generate wild-type AAV.

For purposes of clarity, and not by way of limitation, the detailed description of the invention will be divided into the following sections.
 i) The Vector/Helper DNA Relationship
 ii) Recombinant AAV Vectors
 iii) Helper AAV DNA
 iv) Production of Helper-Free rAAV Stocks
 v) Utility of Helper-Free rAAV Stocks

5.1 THE VECTOR/HELPER AAV VIRUS RELATIONSHIP

According to the present invention, helper-free stocks of recombinant AAV are generated using functionally related recombinant DNA vector and helper AAV DNA constructs.

The rAAV vector of the invention comprises a recombinant AAV genome (the vector) which contains a foreign DNA sequence and is used to cotransfect eukaryotic cells together with helper AAV DNA in the presence of helper virus. According to the present invention, only the rAAV vector is successfully replicated and packaged into infectious virions by said transfected eukaryotic cells, resulting in helper-free AAV vector stocks.

The helper AAV DNA of the invention comprises a recombinant AAV genome which complements the functions necessary for replication and packaging of the rAAV vector, but shares no AAV sequences with the vector. The helper AAV DNA should be unable to replicate and/or unable to be packaged into virions to a measurably significant degree. The inability of the helper AAV DNA to either recombine with rAAV vector sequences or itself form infectious virions is the crux of the present invention.

In order to facilitate construction of rAAV vector and helper AAV DNA sequences, a recombinant AAV molecule may be designed so as to provide convenient cleavage sites which may be used to create "cassettes" of AAV sequence which may, when used in different combinations, be used to generate vector or helper DNA constructs. For example, in a specific embodiment of the invention, psub201 may be used to derive both rAAV vector and helper recombinant molecules (as described more fully in Samulski et al., 1987, J. Virol. 61:3096-3101, which is incorporated in its entirety by reference herein). psub201 comprises an infectious AAV genome inserted into plasmid pEMBL8, and contains engineered XbaI cleavage sites that flank the viral coding domain which do not affect replication of the virus and which allow nonviral sequences to be inserted between the cis-acting viral terminal repeats; the entire viral genome is flanked by PvuII cleavage sites that allow the entire infectious viral chromosome to be excised from plasmid sequences in vitro. According to the invention, a foreign DNA sequence may be inserted between the XbaI sites, leaving intact the AAV termini present in the two flanking PvuII-XbaI fragments. The resulting rAAV vector is capable of integrating into a host genome; complementary viral functions may be supplied by a helper DNA formed by inserting non-AAV sequences in the PvuII-XbaI flanking terminal regions, leaving the coding region between the two XbaI sites intact. The resulting helper DNA shares no common DNA sequences with the corresponding rAAV vector thereby precluding the generation of wild-type virus by homologous recombination. In a specific embodiment of the invention, as exemplified by Section 6, infra, adenovirus terminal sequences may be inserted into the Pvu II - XbaI site in the place of the AAV terminal repeats. The resulting helper DNA was itself found to be unable to replicate, but provided sufficient AAV functions to allow high levels of replication of rAAV vector molecules and production of helper free-stocks of rAAV virions. According to this disclosure, other modified AAV molecules used to derive rAAV vector or helper AAV DNA, bearing different combinations of restriction enzyme sites at different, or similar regions of the AAV genome, may be constructed by one skilled in the art.

5.2 RECOMBINANT ADENO-ASSOCIATED VIRUS VECTORS

The recombinant AAV (rAAV) vectors of the present invention include any recombinant DNA molecule which incorporates sufficient regions of the wild-type AAV genome to permit replication of DNA, normal integration into, as well as excision from, the host cell genome, and should include a cis-acting packaging element. The rAAV vector itself need not contain AAV genes encoding proteins, including those associated with DNA or RNA synthesis or processing or any step of viral replication including capsid formation. In preferred embodiments of the invention, the rAAV vector retains only terminal AAV sequences necessary for integration, excision, replication, and packaging; comprising less than about 195 base pairs of the AAV terminus. In a specific embodiment of the invention, recombinant viruses were generated that contained only 191 nucleotides of the AAV chromosome, and were derived from plasmid psub201 DNA, as described in Samulski et al. (1987, J. Virol. 61: 3096-3101) which is incorporated by reference in its entirety herein.

According to the invention, the rAAV vector may be propagated in microorganisms, for example, as part of a bacterial plasmid or bacteriophage, in order to obtain large quantities of rAAV DNA which may be utilized according to recombinant DNA methodology to generate novel constructions. In a specific embodiment of the invention, the vector is pEMBL8(+).

The rAAV vector of the present invention may incorporate any foreign DNA sequence, including genes or portions of genes. It may be desirable to incorporate a gene with a readily detectable product (known in the art as a marker, recorder, or reporter gene) as part of the rAAV vector although the invention is not limited to such constructs. Readily detectable reporter genes may produce either tumorigenic or non-tumorigenic products. Tumorigenic reporter genes could be utilized, but might present a significant health risk due to their oncogenicity. Non-tumorigenic reporter genes would include, but are not limited to, $\beta$-galactosidase, neomycin phosphoro-transferase, chloramphenicol acetyltranferase, thymidine kinase, luciferase, $\beta$-glucuronidase, and xanthine-guanine phosphoribosyl transferase, to name but a few.

According to the invention, if the foreign DNA of the rAAV vector is to be expressed in host cells, a transcriptional control element, also called a promoter/enhancer sequence, should be provided. The promoter/enhancer sequence may be widely active or may, alternatively, be tissue specific. The promoter/enhancer sequence may be derived from a non-AAV source or may be an AAV promoter provided that no sequences are shared by helper AAV DNA. Promoter/enhancer sequences which might be used to control foreign gene expression, provided for in the present invention, include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpesvirus thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alphafetoprotein gene control region which is active in liver (Krumlauf et al., 1985, 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340, Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

The desirable size of inserted non-AAV or foreign DNA is limited to that which permits packaging of the rAAV vector into virions, and depends on the size of retained AAV sequences. AAV-2 is 4675 base pairs in length (Srivastava et al., 1983, 5. Virol. 45:55-564). Tratschen et al. (1984, Mol. Cell. Biol. 4:2072-2081) constructed an AVBcCAT AAV genome that was 3 percent (approximately 150 nucleotides) longer than the wild-type AAV genome, and found that AVBcCAT could be packaged into virions. An AAV genome too large to be packaged resulted from insertion of a 1.1 kilobase pair fragment of bacteriophage A inserted into a nonessential region of AAV (Samulski and Shenk, personal communication, cited in Hermonat and Muzyczka, Proc. Natl. Acad. Sci. U.S.A. 81:6466:6470). Thus, the total size of the rAAV to be packaged into virions should be about 4800-5000 nucleotides in length.

It may be desirable to exclude portions of the AAV genome in the rAAV vector in order to maximize expression of the inserted foreign gene. For example, it has been observed (Hermonat and Muzyczka, 1984, Proc. Natl. Acad. Sci. U.S.A. 81:6466–6470; Lebkowski et al., 198, Mol. Cell. Biol. 8:3988–3996; Tratschin et al., 1985, Mol. Cell. Biol. 5:3251–3260) that the number of drug-resistant colonies produced by transduction generally did not increase linearly as the multiplicity of AAV recombinant virus was increased. This may have resulted, at least in part, from the inhibitory effects of AAV-coded rep functions. In contrast, using the helper-free rAAV stock of the present invention, wherein the rAAV vector carried the gene for neomycin resistance (see Section 6, infra, and Table II) the number of drug-resistant transductants responded almost linearly to the input multiplicity of recombinant virus. Therefore, it may be desirable to exclude rep encoding sequences from the rAAV vector, as was done in the specific embodiment of the invention described herein.

5.3. HELPER ADENO-ASSOCIATED DNA

The helper AAV DNA of the present invention i) provides viral functions necessary for the replication of rAAV vector and its packaging into infectious virions ii) shares no AAV sequences with rAAV vector, and iii) is not itself replicated or assembled into viral particles to a measurable degree. The helper AAV DNA may contain the entire coding region of the AAV genome or a portion thereof, provided that the above requirements, i–iii), are met.

According to the invention, helper AAV DNA may be propagated in microorganisms, for example, as part of a bacterial plasmid or bacteriophage. Portions of the AAV genome may be incorporated into a recombinant plasmid, bacteriophage, etc. by methods well known in the art. In a specific embodiment of the invention, the vector is pEMBL8(+).

In order to provide viral functions necessary for the replication of rAAV vector and its packaging into infectious virions, the helper AAV DNA must contain cis-acting elements which promote the transcription of desirable viral gene products; such elements may be AAV or non-AAV derived and include but are not limited to the promoter sequences listed in section 5.2, supra. Sequences which facilitate the translation of AAV proteins may also be included.

Any sequences may be incorporated into the helper AAV virus that may be utilized to increase production of rAAV vector virions. Accordingly, transcriptional enhancer or repressor elements may be incorporated into the helper DNA, including, but not limited to, such elements derived from AAV or adenovirus.

The helper AAV DNA cannot itself be incorporated into infectious virions to any significantly measurable degree. According to the invention, helper DNA can be excluded from virion formation by virtue of i) failure to replicate to form a discrete recombinant AAV genome and ii) failure to be packaged into infectious virions. Methods of preventing packaging of rAAV helper DNA include constructing a rAAV helper DNA genome prohibitively large, for example, greater than approximately 5.8 kilobase pairs in length or constructing an rAAV helper DNA which lacks a cis-acting packaging sequence.

In a specific embodiment of the invention, a rAAV helper DNA may be constructed by removing the AAV terminal sequences of psub201 (Samulski et al., 1987, J. Virol. 61:3096–3101, incorporated by reference herein) from the Xba I - Pvu II sites and by inserting, into each of the Xba I sites, an Eco RI - Xba I fragment consisting of the 107 terminal base pairs of adenovirus type 5 DNA using methods known in the art. Unexpectedly, the introduction of the adenovirus sequences has been observed to result in a high efficiency of replication of rAAV vector in cotransfected cells (see Section 6, infra).

In an additional embodiment of the invention, the AAV helper DNA may be incorporated into a cell line, thus bypassing the need to cotransfect AAV helper DNA and rAAV vector sequences. Instead, transfection of the AAV helper DNA-containing cell line with rAAV vector DNA plus infection with the helper adenovirus would directly result in production of helper-free rAAV virus. The present invention provides for such AAV helper DNA-containing cell lines, which may be created by transfecting a cell line permissive for AAV growth with AAV helper virus DNA, and then identifying cells which have stably integrated the transfected DNA sequences, either by identifying cells which express AAV proteins or any other gene, i.e. a reporter gene incorporated into the AAV helper virus DNA or cotransfected with it. The presence of AAV helper virus sequences may be corroborated by propagating selected cells, and then testing for AAV helper virus sequences by hybridization techniques, i.e. Southern blot, , "dot blot" etc. It may be desirable to control the expression of AAV gene products if their expression proves to be toxic to the transfected cells. For example, and not by way of limitation, the expression of AAV products from the helper AAV virus DNA may be put under the control of an inducible promoter/enhancer. For example, the mouse mammary tumor virus promoter/enhancer, which may be induced by treatment with glucocorticoids, may be used to control expression of AAV products; cells carrying this construct would normally express low levels of AAV products, but could be induced to higher levels of expression with dexamethasone prior or simultaneous to introduction of rAAV DNA.

5.4. PRODUCTION OF HELPER-FREE RECOMBINANT AAV STOCKS

The phrase "helper-free recombinant AAV stocks", according to the invention, is construed to mean stocks of infectious virions which contain, virtually, only rAAV vector (as defined supra and in section 3.1) and contain no significant quantities of wild-type AAV or undesirable recombinant AAV (presumably derived from rAAV helper DNA sequences).

According to the method of the invention, helper-free recombinant AAV may be produced by cotransfecting an appropriate cell type with rAAV vector and helper AAV DNA, in the presence of a helper virus, such as adenovirus or herpes virus.

Cotransfection may be performed by the DEAE-dextran method (McCutchen and Pagano, 1968, J. Natl. Cancer Inst. 41:351–357), the calcium phosphate procedure (Graham et al., 1973, J. Virol. 33:739–748) or by any other method known in the art, including but not limited to microinjection, lipofection, and electroporation. Cotransfection may be accomplished using helper virus infected cells, or may be performed simultaneously with, or prior to, viral infection. If adenovirus is used as helper virus, a desirable multiplicity of infection may be between about 5 and 10. Amounts of rAAV vector and helper DNA used in transfection are approximately 0.2 to 10 μg of DNA per $10^6$ cells, but may vary among different DNA constructs and cell types. Cells suitable for transfection of recombinant AAV include any cell line permissive for AAV infection, including, but not limited to HeLa cells or human 293 cells (human embryonic kidney cells transformed with a fragment of adenovirus 5 DNA).

Several days following transfection, a rAAV virus stock may be generated by i) producing a cell lysate, ii) inactivating helper virus (for example, heat inactivation of adenovirus at about 56° C. for approximately 30–45 minutes), and iii) purifying rAAV virions from other elements of the cell lysate according to methods known in the art, such as ultracentrifugation using, for example, a cesium chloride gradient.

Corroboration of the helper-free nature of the resulting rAAV stock may be accomplished by the isolation of low-molecular weight DNA according to the method of Hirt (1967, J. Mol. Biol. 26:365–369), with subsequent evaluation for the presence of appropriate DNA sequences, using methods well known in the art.

5.5. UTILITY OF HELPER-FREE RECOMBINANT AAV STOCKS

The helper-free recombinant AAV stocks produced according to the method of the invention may then be used to infect any cell permissive for AAV infection, including primary cells, established cell lines, a tissue, or an organism. It has been shown that introduction of rAAV by infection (using virions) is about two orders of magnitude more efficient than transfection with rAAV DNA (Tratshen et al., 1985, Mol. Cell. Bio. 5:3251–3260). The method of the invention thereby provides a more efficient means of introducing a rAAV which is virtually free of contaminating AAV into host cells. Prior to the invention, viral stocks were found to be contaminated, to various degrees, with helper sequences, and therefore the purity of rAAV construct being introduced into the cells by infection could not be assured.

In order to identify cells which, consequent to rAAV infection, express foreign DNA sequences, it may be desirable to incorporate a gene which encodes a selectable or detectable product, for example, the neomycin resistance gene (Southern and Berg, 1982, J. Mol. Appl. Genetics 1:327–341) or the hygromycin resistance gene (Blothlinger and Diggelmann, 1984, Mol. Cell. Biol. 4:2929–2931).

The capability to produce helper-free rAAV stocks enables the execution of techniques which were inefficient or impossible in the presence of contaminating AAV sequences. Since wild-type AAV is not present to inhibit high efficiency transformation of cells infected with the rAAV virion stock, nearly all of the cells exposed to rAAV can be infected (Table III). The rAAV DNA can then be integrated into the chromosomes of recipient cells. This high efficiency gene transfer may be especially useful if one wishes to introduce a foreign DNA sequence into a rare cell type within a mixed cell population. Rare stem cells within the total population of hematopoietic cells obtained from the bone marrow of an animal or a human are an example of such a rare cell type. Since the rAAV virion stock can successfully infect nearly all cells within a population, rare stem cells may be successfully infected.

In a specific embodiment of the invention, it was, unexpectedly, found that the replacement of the AAV terminal repeated sequences with adenovirus 5 DNA sequences resulted in a high level of replication of rAAV vector in cotransfected cells.

According to a specific embodiment of the invention, a rAAV vector which lacks all rAAV coding sequences (and therefore maximizes the potential size of foreign DNA transduced) can be used to produce pure viral stocks and, surprisingly, despite its minimal amount of AAV sequence, can successfully integrate in rescuable form into cellular chromosomes.

In addition, the ability to produce helper-free stocks of rAAV enables more controlled rescue of incorporated AAV provirus, requiring addition of both wild-type AAV and adenovirus. Prior to the method of the invention, because of contaminating helper AAV virus, rescue of provirus could proceed in a less controlled manner, requiring only helper adenovirus.

Finally, the method of the invention significantly augments the utility of adeno-associated virus as a transducing vector. The broad host range, capacity to readily insert and/or be excised from cellular DNA, ability to act as part of a "shuttle vector" between prokaryotic and eukaryotic cells, and effective absence of pathogenicity are advantages of the AAV transducing system hitherto offset by the inability to generate helper-free virus. The method of the invention overcomes the obstacle presented by contaminated viral stocks, and allows for expansion of the rAAV transducing vector system. In the future, rAAV may prove to be the vector of choice for gene transfer into organisms.

6. EXAMPLE: HELPER-FREE STOCKS OF RECOMBINANT ADENO-ASSOCIATED VIRUSES (AAV): NORMAL INTEGRATION DOES NOT REQUIRE VIRAL GENE EXPRESSION

Recombinant AAV virus stocks invariably have been contaminated with helper AAV virus used to provide acting functions required for AAV replication and encapsidation. In this report we describe a method for production of recombinant AAV virus stocks that contain no detectable wild-type helper AAV virus. The recombinant viruses contain only the terminal 191 nucleotides of the viral chromosome, demonstrating that all cis-acting AAV functions required for replication and virion production are located within that region. Helper-free virus stocks were able to stably introduce a drug-resistance marker gene into a high percentage (70%) of infected cells. Recombinant viral DNAs carrying a drug resistance marker gene were integrated into the cellular genome and then excised and replicated when the cells were subsequently infected with wild-type AAV plus adenovirus. Thus, the AAV termini are sufficient for normal integration of the AAV chromosome into a host cell genome. No AAV gene expression is required to establish a latent infection.

6.1. MATERIALS AND METHODS

6.1.1. PLASMIDS AND VIRUSES psub201 (Samulski et al., 1987, J. Virol. 61:3096–3101), an infectious clone of AAV type 2 DNA, served as the parent to all plasmid constructs described in this report. pAAV/neo and pAAV/hyg were prepared by substituting the AAV coding region in psub201 with either the neomycin-resistance gene (Southern and Berg, 1982, J. Mol. Appl. Genetics 1:327–341) or hygromycin resistance gene (Blochinger and Diggelman, 1984, Mol. Cell. Biol. 4:2929–2931) controlled by the SV40 early promoter. The drug-resistance genes were substituted between the two XbaI sites present in psub201 to generate recombinant viral DNAs in which 191 bp segments from the termini of sub201 bracket either the neomycin- or hygromycin-resistance gene. pAAV/no-tr was generated by deleting the 191 base pair AAV termini from psub201 DNA using XbaI and PvuII cleavage sites which bracket the terminal segments. pAAV/Ad was produced by inserting into each of the two XbaI sites of pAAV/no-tr an EcoRI-XbaI fragment consisting of the 107 terminal base pairs of adenovirus type A DNA which were derived from a cloned, left-terminal fragment of the viral chromosome.

sub201 is a phenotypically wild-type derivative of AAV type 2 (Samulski et al., 1987, J. Virol. 61:3096–3101). AAV/neo and AAV/hyg virus stocks were generated by cotransfection of adenovirus-infected cells with pAAV/neo or pAAV/hyg plus pAAV/Ad. The concentration of sub201, AAV/neo or AAV/hyg virus particles in virus stocks was determined by extracting and quantifying DNA from a known volume of virus stock. A virus lysate was heat-treated at 56° C. for 30 min to inactivate the adenovirus, treated with DNaseI (10 µg/ml) at 37° C. for 15 min to degrade nonvirion DNA, heated at 68° C. for 10 min to inactivate DNase I, treated with proteinase K (100 µg/ml) in SDS (0.1%) at 37° C. for 3 hrs, and then nucleic acids were extracted with phenol/chloroform and precipitated with ethanol. DNA was resuspended in low salt buffer, denatured by boiling, diluted into 10 volumes of ice cold 10 ×SSC (1×SSC is 0.15M NaCl, 0.015M sodium citrate), applied to a nitrocellulose sheet using a dot blot apparatus and probed using a [$^{32}$P]labeled DNA common to all three viruses (AAV terminal sequence). The intensities of dots were compared to those of standard curve generated by assaying dilutions of an AAV DNA preparation of known concentration.

6.1.2. CELL CULTURES

HeLa cells were from the American Type Culture Collection (Rockville, Md.). Detroit 6 cells are a human lung carcinoma cell line (Berman et al., 1955, Blood 10:896–911) that do not contain integrated AAV sequences (Berns et al., 1975, Virology 68:556–560). Both cell lines were propagated in medium containing 10% calf serum.

6.1.3. DNA REPLICATION AND EXCISION ASSAYS

To assay AAV-specific DNA replication, HeLa cells were transfected with circular plasmid DNAs by the DEAE-dextran procedure (McCutchan et al., 1968, J. Natl. Cancer Inst. 41:351–357). 1.0 µg of each DNA (recombinant and helper) was included in the transfection mixtures as well as adenovirus type 5 virions at a multiplicity of 10 pfu/cell. Excision and rescue was assayed by infection of AAV-containing Detroit 6 cells with either adenovirus alone or with both adenovirus plus wild-type AAV (sub201). For both replication and excision/rescue assay, low molecular-weight DNA was isolated by the procedure of Hirt (1967, J. Mol. Biol. 26:365–369 at 40 hr after transfection/infection, and analyzed by DNA blot analysis for the presence of AAV-specific DNAs.

6.1.4. DNA BLOT ANALYSIS

High molecular weight DNA was prepared, 10 µg portions were digested with the appropriate restriction enzymes, digests were fractionated by electrophoresis on a 1% agarose gel, transferred to nitrocellulose, and hybridized using [$^{32}$p] labeled probe DNAs prepared by nick-translation (Maniatis et al., 1982 in "Molecular Cloning, a laboratory manual" Cold Spring Harbor Laboratory, Cold Spring Harbor, N.Y.).

6.1.5. PROTEIN ANALYSIS

For analysis of AAV capsid proteins, HeLa cells were simultaneously transfected with AAV-specific plasmid DNAs by the calcium phosphate procedure (Graham et al., 1973, Virology 52:456–467) and infected with adenovirus. Cultures were labeled for 1 hr with [$^{35}$S]methionine (100 µCi/ml; 1,100 Ci/mmole) 40 hr later and then subjected to immunoprecipitation with a monoclonal antibody prepared against purified AAV capsid proteins (L.-S. Chang, S. Pan. R. J. Samulski and T. Shenk, in preparation). Immunoprecipitation and electrophoresis were as previously described (Sarnow et al., 1982, Cell 28:387–394).

6.1. RESULTS

6.2.1. RECOMBINANT AAV STOCKS THAT CONTAIN NO DETECTABLE HELPER AAV

We wished to determine whether AAV gene expression is required for normal integration of AAV DNA into the genome of a host cell. To ask this question, two conditions had to be met. First, it was necessary to construct a recombinant virus that contained cis-acting but no trans-acting AAV functions. Second, it was necessary to generate a stock of the recombinant virus containing no helper AAV particles that could provide trans-acting functions during a subsequent infectious cycle.

Cis-acting AAV sequences appear to reside entirely in and near the terminal repeated sequences at the ends of the viral chromosome (McLaughlin et al., 1988, J. Virol. 62:1963–1973). Therefore, two recombinant viruses were produced that contained AAV termini bracketing marker genes.

psub201 DNA (Samulski et al., 1987, J. Virol. 64:3096–3101 was used as a recipient for non-viral sequences. This is an infectious clone of AAV whose virus-specific insert (FIG. 1A) differs from wild-type AAV in that two XbaI cleavage sites have been added at sequence positions 190 and 4484, and the right-end 191 base pairs of the viral DNA (the XbaI site at position 4484 to the right terminus) have been substituted for the left-end 190 base-pair domain (left terminus to the XbaI site at position 190). Since the viral DNA includes terminal repeats of 145 base pairs, the modification results in the substitution of 46 base pairs unique to the right-end domain of the AAV chromosome (sequence position 4485 to 4530) for 45 base pairs present near the left end (sequence position 146 to 190). When HeLa cells were transfected with psub201 DNA in the presence of adenovirus, the AAV chromosome was excised from plasmid sequences and replicated normally (Samulski et al., 1987, J. Virol. 61:3096–3101).

The pair of XbaI cleavage sites in psub201 provided the opportunity to substitute the entire AAV coding region with non-viral sequences which were then bracketed by the AAV terminal repeats. Either the neomycin-resistance or hygromycin-resistance coding regions regulated by the SV40 early transcriptional control region was substituted for the AAV coding region to produce pAAV/neo (FIG. 1A) and pAAV/hyg, respectively. These recombinant constructs contained the known AAV cis-acting but no trans-acting functions.

Two helper DNAs were produced. The first was termed pAAV/no-tr (no terminal repeat) since it contained only the AAV coding sequences internal to the XbaI cleavage sites of psub201. The second was termed pAAV/Ad since it contained the adenovirus type 5 terminal sequence (107 bp) in place of the normal AAV termini (FIG. 1A). Neither helper DNA could be packaged into AAV virions since they lacked the terminal cis-acting domain required for this function, and neither construct contained sequences present in pAAV/neo or pAAV/hyg, precluding homologous recombination between helper and recombinant viral DNAs.

pAAV/no-tr and pAAV/Ad were compared to wild-type AAV DNA (psub201) for their ability to provide helper function to pAAV/hyg (Table 1). pAAV/hyg, as circular plasmid DNA, was transfected into HeLa cells together with various helper plasmids in the presence of adenovirus (dl309, 10 pfu/cell). When maximal cytopathic effect occurred (72 hr), cultures were harvested, freeze-thawed three times, and heat treated (56° C, 45 min) to inactivate adenovirus. Dilutions of the lysates were then used to infect subconfluent HeLa cells, and hygromycin-resistant ($Hyg^R$) colonies were selected.

TABLE I

| AAV/hyg Yields Produced Using Various Helper Plasmids to Provide Transacting AAV Functions. | |
|---|---|
| Helper Plasmid | $Hyg^R$ Colonies/ml Lysate |
| pAAV/no-tr | $3 \times 10^2$ |
| AAV/Ad | $3 \times 10^4$ |
| psub201 | $5 \times 10^5$ |

By this assay, psub201 DNA was the most efficient helper. pAAV/no-tr was very inefficient, while pAAV/Ad performed at an intermediate level. Contransfection with pAAV/Ad DNA generated a yield of AAV/hyg virus reduced by a factor of 10–20 as compared to stocks generated by cotransfection with psub201 DNA. It produced $3 \times 10^4$ hygromycin-resistant colonies per ml lysate (Table I).

Accumulation of AAV-specific DNAs was monitored in HeLa cells infected with adenovirus and simultaneously cotransfected with pAAV/neo DNA and either psub201 or pAAV/Ad helper DNA (FIG. 1). Low-molecular-weight DNAs were extracted at 40 hr after infection/transfection and subjected to DNA blot analysis. The blots were first probed using a [$^{32}$P]labeled DNA comprising AAV coding sequences which detected helper virus DNAs but not AAV/neo DNA (FIG. 1B). Analysis with this probe indicated that AAV helper DNA was excised and amplified in cells transfected with psub201 DNA but not pAAV/Ad DNA. The adenovirus termini could not substitute for the cis-acting functions present in AAV termini. Next, the blots were probed using a [$^{32}$P]labeled DNA comprising coding sequences from the neomycin-resistance gene which detected AAV/neo DNA but not helper virus DNAs (FIG. 1C). The recombinant viral DNA was excised from pAAV/neo DNA and amplified to a similar extent in the presence of either helper virus.

The AAV/neo stocks obtained using either pAAV/Ad or psub201 DNA as helper were then used to infect HeLa cells in the presence of adenovirus. The recombinant virus stock prepared using psub201 DNA as helper produced replicating AAV/neo DNA (FIG. 1B and C, P2), since the stock also contained sub201 virus to provide AAV helper functions. In contrast, the recombinant virus stock prepared using pAAV/Ad DNA as helper did not generate replicating AAV/neo DNA (data not shown). This makes sense since this stock was predicted to contain no helper virus to provide transacting AAV functions. To further confirm that no helper virus was present in stocks of AAV/neo prepared using pAAV/Ad as helper DNA, a stock of the recombinant virus was subjected to equilibrium density centrifugation, fractions were collected, and probed for the presence of neo and AAV coding sequences (FIG. 2). Only neo coding sequences were detected in the portion of the gradient (fractions 9, 10, and 11) containing virions.

pAAV/Ad was originally constructed to test the possibility that the adenovirus termini might mediate replication of the AAV sequences in the presence of the adenovirus helper virus. If the adenovirus termini mediated any amplification of AAV/Ad sequences, it was with poor efficiency since AAV/Ad DNA was not detected in the DNA blot analysis described above (FIG. 1B). Nevertheless, pAAV/Ad served as a significantly better helper than pAAV/no-tr (Table I).

Even though AAV/Ad DNA was not detectably amplified, AAV gene products were expressed at higher levels in cells transfected with pAAV/Ad than those receiving pAAV/no-tr. This was demonstrated by immunoprecipitation of AAV capsid proteins from cells labeled with [$^{35}$S]methionine for 1 hr beginning at 40 hr after transfection (FIG. 3). Cells infected with adenovirus and transfected with pAAV/Ad DNA produced nearly as much AAV capsid protein as cells that received the infectious AAV clone, psub201. This probably results from enhanced transcription of the AAV genome in the presence of transcription-promoting elements within the adenovirus terminal repeats (Hearing and Shenk, 1983, Cell 33:695–703).

6.2.2. NORMAL INTEGRATION OF RECOMBINANT DNAS IN THE ABSENCE OF AAV GENE EXPRESSION

Using pAAV/Ad DNA as a helper, it was possible to generate stocks of recombinant viruses that contained no helper virus. The amount of recombinant virus in these stocks was determined by quantitation of hybrid DNA extracted from virions (see Section 6.1, Materials and Methods). It was also possible to quantitate the recombinant virus using a biological assay (Table 2). pAAV/neo was transfected into HeLa cells together with pAAV/Ad helper plasmid in the presence of adenovirus (dl309, 10 pfu/cell). When maximal cytopathic effect occurred, cultures were harvested, freeze-thawed three times and then heat treated (56° C., 45 min) to inactivate adenovirus. The concentration of AAV/neo particles in the resulting stock was then determined by dot blot analysis using dilutions of known AAV DNA concentrations to establish a standard curve. AAV/neo was then used to infect subconfluent HeLa cells in the presence or absence of sub201, and G418-resistant ($G418^R$) colonies were selected. Each value presented in the table is the average of 10 independent transduction mixtures of $10^4$ cells each. The number of colonies increased in proportion to the input multiplicity of AAV/neo virions (Table 2, experiment 1).

TABLE II

AAV/neo Transformation of HeLa Cells in the
Absence and Presence of Helper Virus to Provide
Trans-Acting AAV Functions

| AAV/neo (Particles) | sub201 (Particles) | G418$^R$ Colonies/$10^4$ cells |
|---|---|---|
| Experiment 1. | | |
| $10^3$ | — | 2 |
| $10^4$ | — | 18 |
| $10^5$ | — | 85 |
| Experiment 2. | | |
| $10^4$ | — | 51 |
| $10^4$ | $10^3$ | 92 |
| $10^4$ | $10^4$ | 220 |
| $10^4$ | $10^5$ | 87 |

The number of G418-resistant colonies could be increased further when the input multiplicity of AAV/neo virus was held constant and increasing amounts of wild-type AAV (sub201) were added to the infecting mixture (Table II, experiment 2). However, the maximal enhancement was only 4-fold, and the total number of drug-resistant colonies decreased at the highest input levels of sub201. Thus, the efficiency of transduction by AAV/neo virions was not greatly enhanced by the presence of trans-acting AAV functions.

The highest multiplicity of AAV/neo virus used in the previous experiments was 10 particles/cell. About 20 to 100 wild-type AAV particles constitute a single infectious unit (McLaughlin et al., 1988, J. Virol. 62:1963-1973; Tratschin et al., 1985, Mol. Cell. Biol. 5:3251-3260). Thus it seemed possible that the efficiency of transduction could be enhanced by increasing the input multiplicity of recombinant virions in the absence of helper virus. Accordingly, AAV/neo virus particles from 30 plates (10 cm diameter) of 293 cells transfected with pAAV/neo plus pAAV/Ad and infected with adenovirus were purified and concentrated by equilibrium density centrifugation, the gradient was fractionated, aliquots were dialyzed into tris-buffered saline, and the concentration of AAV/neo particles in peak fractions was determined by dot blot analysis as described in the legend to Table II. A total of approximately $1 \times 10^8$ AAV/neo particles was obtained. The concentrated stock was then used to infect $10^4$ Detroit 6 cells at a multiplicity of 1000 particles/cell. 24 hr later, cells were removed from the plate, counted and plated at the cell densities indicated. After an additional 24 hr. G418 was added. Drug-resistant colonies were counted two weeks later. Approximately 70% of the infected cells gave rise to G418-resistant colonies (Table III).

TABLE III

Transduction of Detroit 6 Cells with AAV/neo
Virions at a High Multiplicity of Infection in
the Absence of Helper Virus.

| Number of Infected Cells | Number of G418-Resistant Colonies |
|---|---|
| $9 \times 10^3$ | >6000 |
| $1 \times 10^3$ | 650 |
| $1 \times 10^2$ | 72 |

Thus, the efficiency of transduction can be dramatically increased by infecting with recombinant virus at high multiplicity in the absence of helper virus.

Next, the physical structure of the AAV/neo chromosome was examined in G418-resistant cell lines. 17 drug-resistant clones were prepared from Detroit 6 cells infected with helper-free AAV/neo virus. No AAV DNA was detected by DNA blot analysis of low-molecular-weight DNA prepared from the cell lines by the procedure of Hirt, 1967, J. Mol. Biol. 26:365-369 (data not shown). AAV sequences were present in very large DNA fragments when high molecular weight cellular DNA was subjected to DNA blot analysis (data not shown). Further, detailed DNA blot analysis of three non-rescuable and one rescuable cell line (FIG. 5B, discussed below), revealed fragments of appropriate size to represent viral/host DNA junctions. Therefore, the AAV/neo DNA present in each of the cells lines was almost certainly integrated into the host cell chromosome.

Normally AAV DNA can be induced to excise from the host cell chromosome and replicate by infection with adenovirus. As expected, AAV/neo DNA was not rescued from any of the 17 lines by infection with adenovirus alone (data for 7 lines is displayed in FIG. 4). AAV/neo DNA was rescued from 7/17 lines by coinfection with both wild-type AAV (sub201) and adenovirus (FIG. 4). This experiment supported the earlier conclusion that no wild-type AAV was present in the AAV/neo virus stock since none was present in any of the drug-resistant cell lines. Further, it demonstrated that AAV/neo DNA could be "properly" integrated in the absence of AAV gene expression in the sense that it could be excised when AAV plus adenovirus-coded products were subsequently provided.

Figure 5A:
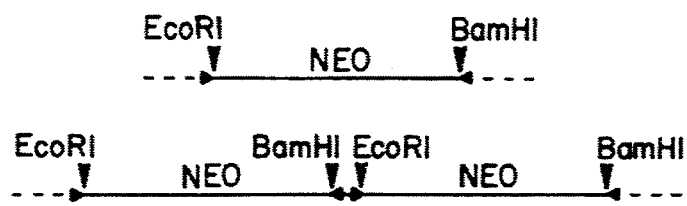
Figures 5B, 5C:
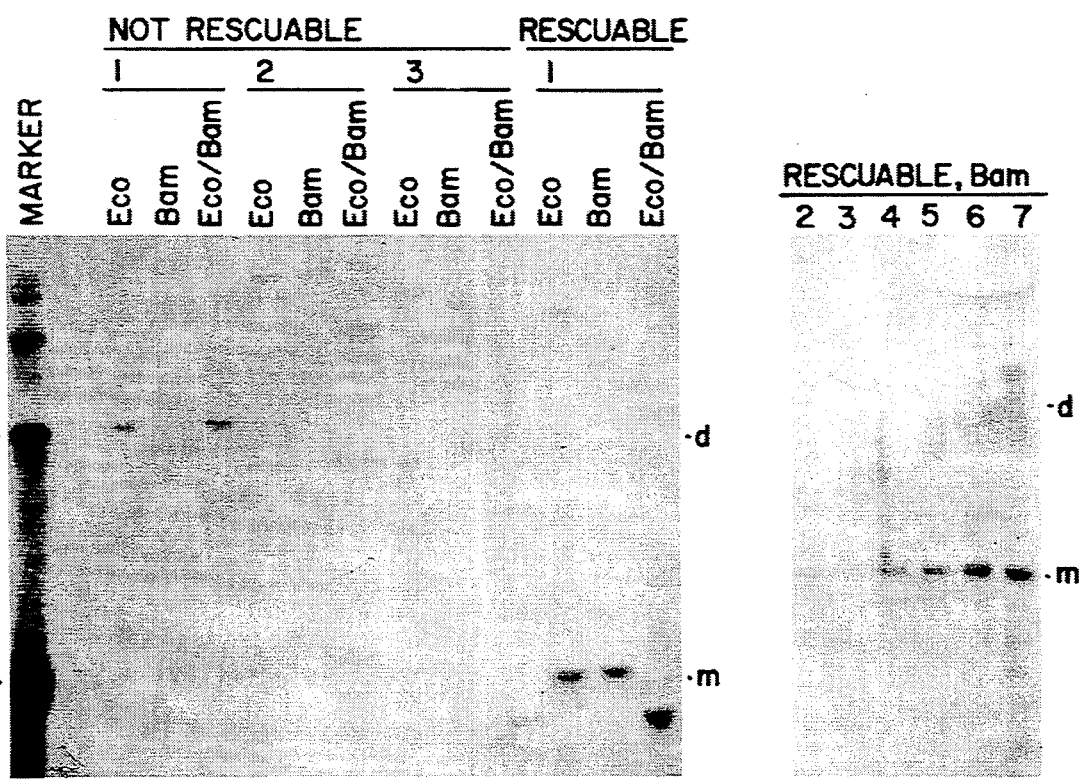

AAV DNA which has integrated into the cellular chromosome in a rescuable state often exists as head-to-cell concatemers (Cheung et al., 1980, J. Virol. 3.3:739-748; Laughlin et al., 1986, J. Virol. 60:515-524; McLaughlin et al., 1988, J. Virol. 62:1963-1973). DNA blot analysis was performed to determine whether this was also the case for cell lines that harbored rescuable AAV/neo DNA (FIG. 5). Head-to-tail concatemers of AAV/neo DNA can be identified by digestion of high molecular weight DNA with the EcoRI and BamH1 endonucleases. Head-to-tail concatemers will generate unit-length DNA when cleaved with only one of the two enzymes and a shorter than unit-length fragment when cleaved with both (FIG. 5A). Inserts of single AAV/neo molecules or head-to-head concatemers will not generate the predicted fragments. Three non-rescuable cell lines contained no detectable head-to-tail concatemers by this assay (FIG. 5B). All seven rescuable cell lines generated AAV/neo DNA fragments of the size predicted for head-to-tail concatemers (FIGS. 5B and C). Thus, rescuable cell lines were generated in the absence of trans-acting AAV function which contain tandemly duplicated molecules of AAV/neo DNA arranged in a head-to-tail orientation.

6.3. DISCUSSION

6.3.1. HELPER VIRUS-FREE STOCKS OF RECOMBINANT VIRUSES.

Earlier studies attempted to minimize the level of contaminating helper AAV viruses in recombinant AAV stocks either by using a helper DNA too large to be encapsidated (Hermonat and Muzyczka, 1984, Proc. Natl. Acad. Sci. U.S.A. 81:6466-6470; McLaughlin et al., 1988, J. Virol. 62:1963-1973) or by employing a helper DNA lacking all or portions of one or both terminal AAV sequences (Lebkowski et al., 1988, Mol. Cell. Biol. 8:3988-3996). However, homologous recombination events between helper and hybrid DNA molecules generated wild-type AAV DNA that could then be amplified and encapsidated.

The experiments reported here demonstrate that it is possible to generate stocks of recombinant AAV virions that do not contain detectable helper virus. This was achieved by employing a helper virus that lacked all known cis-acting AAV replication and encapsidation functions (pAAV/Ad, FIG. 1A). Further, the helper AAV and recombinant AAV DNA pair contained no sequence in common, minimizing the opportunity for recombination that could generate a packageable helper chromosome. The recombinant viruses contained only the right terminal 191 bp of the AAV chromosome bracketing both ends of a foreign DNA (AAD/eno and AAV/hyg, FIG. 1A), while the helper DNA lacked the same terminal sequence (pAAV/Ad, FIG. 1A).

Figures 4A, 4B:
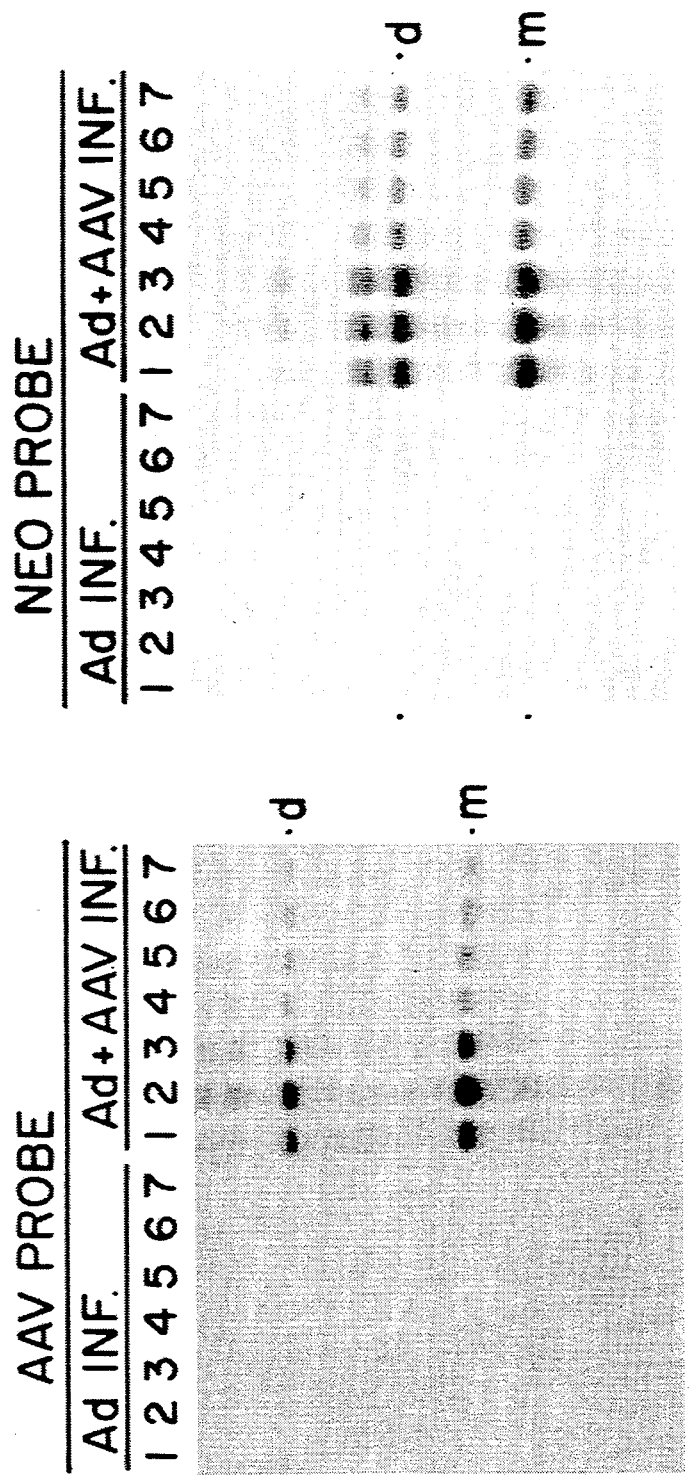

A variety of observations support the conclusion that the stocks of AAV/neo and AAV/hyg contained no detectable helper virus such as AAV/Ad or a wild-type-like virus generated by non-homologous recombination. First, no replication of AAV/Ad DNA or any other molecule containing the AAV coding region was detected in HeLa cells cotransfected with pAAV/Ad and pAAV/neo DNA in the presence of adenovirus (FIG. 1B). Second, the resulting AAV/neo virus stock could not be propagated through a second round of infection by coinfection with adenovirus alone (data not shown), indicating it did not contain any helper or wild-type-like AAV particles to provide trans-acting AAV functions. Third, no AAV coding sequences were detected in peak fractions of AAV/neo virions that were subjected to equilibrium centrifugation in a cesium chloride gradient and then assayed by DNA blot analysis (FIG. 2). Fourth, none of the Detroit 6 cell lines produced by transduction of G418 resistance with the AAV/neo stock contained either rescuable AAV DNA or AAV trans-acting functions (FIGS. 4A and 4B).

The 191 bp segments which included the entire 145 bp terminal repeats of the AAV genome contained the cis-acting signals needed to achieve excision and replication of the recombinant DNAs at normal efficiency subsequent to transfection. AAV/neo DNA accumulated to about the same level as sub201 DNA within transfected HeLa cells (FIGS. 1B and 1C). It is not possible to determine from our present results whether the recombinant genomes were encapsidated at normal efficiency. However, it is clear, given our ability to produce AAV/neo and AAV/hyg virions, that the right end 191 bp of the AAV chromosome (this sequence is present at both ends of the recombinant DNAs) contains sufficient cis-acting information to signal packaging at some level. These constructs further refine the localization of the putative cis-acting AAV packaging element from 284 bp (McLaughlin et al., 1988 supra) to 191 bp (AAV/neo, FIG. 1A).

The AAV terminal sequences were originally substituted with adenovirus terminal sequences in pAAV/Ad since it seemed possible that the adenovirus DNA replication origins present in the terminal sequences would respond to adenovirus-coded replication functions and serve to amplify the helper chromosome. This did not occur at detectable levels either when pAAV/Ad DNA was introduced as a circular DNA (FIG. 1B) or when AAV/Ad sequences were cleaved from the plasmid and used to transfect cells as linear molecules (data not shown). As luck would have it, however, the adenovirus termini substantially enhanced expression of AAV-specific proteins from pAAV/Ad DNA as compared to pAAV/no-tr that contained neither adenovirus nor AAV terminal sequences (FIG. 3). This enhanced expression is likely due to transcriptional enhancing elements believed to preside in the adenovirus terminal repeats (Hearing and Shenk, 1983, Cell 33:695-703).

6.3.2. NORMAL INTEGRATION WITHOUT AAV GENE EXPRESSION.

Earlier studies of drug-resistant cell lines generated by transduction with a stock of recombinant AAV (e.g., AAV carrying a neomycin-resistance gene) containing wild-type helper virus have identified lines that contain a recombinant but no wild-type AAV chromosomes (e.g., McLaughlin et al., 1988, J. Virol. 62:1963-1973). However, it is not possible to be certain from this result whether trans-acting AAV functions were expressed and mediated the integration of the AAV recombinant. Perhaps the original cell received both recombinant and wild-type viruses, and, although the wild-type genome was expressed, only the recombinant chromosome became integrated.

The experiments reported here clearly demonstrate that a recombinant virus (AAV/neo) containing only the terminal 191 bp of the AAV genome can integrate normally, in a rescuable form, in the absence of AAV gene expression. As discussed above, the AAV/neo stocks contained no detectable helper or wild-type-like viruses. The recombinant viral DNA's were judged to be integrated into the cellular genome of drug-resistant cell lines since no viral DNA was detected in preparations of low-molecular-weight DNA, viral sequences were present in high-molecular-weight DNA, and DNA fragments of sizes consistent with virus/host DNA junctions were observed upon DNA blot analysis (FIG. 5B). Two observations indicated that the recombinant viral DNA's were integrated normally. First, the viral sequences in a substantial portion (7/17) of the cell lines tested could be rescued by infection with a mixture of adenovirus and AAV (FIG. 4). Second, all of the rescuable cell lines contained head-to-tail concatemers of the recombinant viral genome. Head-to-tail concatemers have been described for a variety of rescuable AAV inserts (Cheung et al., 1980, J. Viral. 33:739-748; Laughlin et al., 1986, J. Viral. 60:515-524; McLaughlin et al., 1988, J. Viral. 62:1963-1973). As yet it is not clear how they arise since dimerized molecules produced during normal AAV DNA replication are head-to-head or tail-to-tail repeats (Berns, 1984, The Parvoviruses, supra). Our results demonstrate that the mechanism by which head-to-tail concatemers arise does not require AAV gene expression.

The present experiments rule out a requirement for AAV gene expression within an infected cell for normal integration. Although it is clear that integration has occurred in the complete absence of rep functions, we cannot rule out a possible direct role in the process for one or more capsid proteins that enter the cell as structural elements of the virion.

6.3.3. HIGH EFFICIENCY TRANSDUCTION WITH RECOMBINANT VIRUSES

The efficiency with which G418 resistance was transduced by the AAV/neo stock was only slightly enhanced by addition of wild-type AAV to the infecting mixture (at most, 4-fold, Table 2). In fact, high levels of added AAV reduced the efficiency of transduction (Table 2). Functions encoded by the left half of the AAV chromosome (rep functions) have been shown to negatively regulate AAV gene expression under certain conditions (Labow et al., 1986, J. Viral. 60:251-258;

Tratshen et al., 1986, Mol. Cell. Biol. 6:2884–2894) and to interfere with expression of genes regulated by non-AAV control elements, including the SV40 early promoter (Labow et al., 1987, Mol. Cell. Biol. 7:1320–1325). McLaughlin et al. (1988, supra) have recently suggested rep gene products might interfere with efficient expression of non-viral marker genes in recombinant AAV genomes. Our results are consistent with this view. In fact, we were able to achieve a very high frequency of transduction (about 70%) by infecting with AAV/neo at a multiplicity of 1000 particles/cell in the absence of helper virus (Table III).

In general, it is difficult to compare the efficiency of transduction achieved with AAV/neo virus stocks to efficiencies reported by others. Earlier experiments (Hermonat and Muzyczka, 1984, Proc. Natl. Acad. Sci. U.S.A. 81:6466–6470; Lebkowski et al., 1988, Mol. Cell. Biol. 8:3988–3996; McLaughlin et al., 1988, J. Viral. 62:1963–1973; Tratschin et al., 1985, Mol. Cell. Biol. 5:3251-3260) included helper virus in the transduction inoculum, employed different virus constructs and utilized a variety of protocols to select drug resistant cell clones. Further, a variety of methods for quantification of virus particles was employed. Nevertheless, in general, 1 to 3% of cells have been successfully transduced to drug resistance, a frequency considerably lower than that obtained by high multiplicity infection with AAV/neo virions in the absence of helper AAV (Table III).

7. DEPOSIT OF MICROORGANISMS

The following microorganisms containing the indicated recombinant plasmids were deposited on Jul. 25, 1989 with the American Type Culture Collection, 12301 Parklawn Drive, in Rockville, Md.

| Plasmid | Host | ATCC Accession No. |
|---|---|---|
| pAAV/Ad | E. coli DH5a | 68066 |
| pAAV/neo | E. coli DH5a | 68065 |

The present invention is not to be limited in scope by the viruses and recombinant DNA constructs exemplified or deposited microorganisms which are intended as but single illustrations of one aspect of the invention. Indeed, various modifications of the invention in addition to those shown and described herein will become apparent to those skilled in the art from the foregoing description and accompanying figures. Such modifications are intended to fall within the scope of the appended claims.

What is claimed is:

1. A method for producing a helper-free stock of recombinant adeno-associated virus comprising:
   a) cotransfecting cells permissive for adeno-associated virus replication, in the presence of helper virus infection with i) a recombinant adeno-associated virus vector which contains a portion of foreign DNA sequence and which can be incorporated into an infectious virion and ii) a recombinant helper adeno-associated virus DNA which provides viral functions sufficient for the replication and packaging into infectious virions of said recombinant adeno-associated virus vector, and which comprises a nucleotide sequence not found in wild-type adeno-associated virus which promotes expression of adeno-associated virus genes which results in the viral functions provided, but which lacks adeno-associated virus terminal repeat sequence and shares no adeno-associated virus sequences with said vector, and which cannot itself be incorporated into an infectious virion in said cotransfected cells; and
   b) collecting virions produced.

2. The method of claim 1 in which the helper virus is selected from the group consisting of herpesvirus, cytomegalovirus, Epstein-Barr virus, and vaccinia virus.

3. A method for producing a helper-free stock of recombinant adeno-associated virus comprising:
   a) cotransfecting cells permissive for adeno-associated virus replication, in the presence of helper virus infection with i) a recombinant adeno-associated virus vector which contains a portion of foreign DNA sequence and which can be incorporated into an infectious virion and ii) a recombinant helper adeno-associated virus DNA which provides viral functions sufficient for the replication and packaging into infectious virions of said recombinant adeno-associated virus vector, and which comprises adenovirus terminal DNA Sequence but which lacks adeno-associated virus terminal repeat sequence and shares no adeno-associated virus sequences with said vector, and which cannot itself be incorporated into an infectious virion in said cotransfected cells; and
   b) collecting virions produced.

4. The method of claim 2 or 3 in which the recombinant adeno-associated virus vector comprises up to about 195 base-pairs of the adeno-associated virus terminal repeated sequences.

5. The method of claim 2 or 3 in which the recombinant adeno-associated vector lacks adeno-associated virus gene-encoding sequences.

6. The method of claim 2 or 3 in which the recombinant adeno-associated virus vector lacks the adeno-associated virus rep gene.

7. The method of claim 2 or 3 in which the recombinant adeno-associated virus vector comprises a transcriptional promoter not present in wild-type adeno-associated virus.

8. The method of claim 2 or 3 in which the recombinant adeno-associated virus vector is plasmid pAAV/neo, deposited with the ATCC and assigned accession number 68065.

9. The method of claim 2 or 3 in which the recombinant helper adeno-associated virus DNA encodes an adeno-associated virus gene located between nucleotide 195 and nucleotide 4480 of the adeno-associated virus genome.

10. The method of claim 2 or 3 in which the recombinant helper adeno-associated virus DNA is plasmid AAV/Ad, deposited with the ATCC and with the accession number 68066.

11. The method of claim 3 in which the helper virus is selected from the group consisting of herpes virus, cytomegalovirus, Epstein-Barr Virus, and vaccinia virus.

12. A helper-free stock of recombinant adeno-associated virus produced according to the method of claim 4.

13. A helper-free stock of recombinant adeno-associated virus produced according to the method of claim 5.

14. A helper-free stock of recombinant adeno-associated virus produced according to the method of claim 6.

15. A helper-free stock of recombinant adeno-associated virus produced according to the method of claim 9.

16. A method for producing a helper-free stock of recombinant adeno-associated virus comprising:
   a) transfecting a recombinant adeno-associated virus vector, containing a portion of foreign DNA sequence and which can be incorporated into an infectious virion, in the presence of helper virus, into a cell line which comprises recombinant helper adeno-associated virus DNA such that the cell line provides the viral functions sufficient for the replication and packaging into infectious virions of said recombinant adeno-associated virus vector, in which the helper adeno-associated virus DNA comprises a nucleotide sequence not found in wild-type adeno-associated virus which promotes expression of adeno-associated virus genes which results in the viral functions provided but which lacks adeno-associated virus terminal repeat DNA sequence and shares no adeno-associated virus sequences with said vector; and
   b) collecting virions produced.

17. The method of claim 16 in which the recombinant adeno-associated virus vector comprises up to about 195 base-pairs of the adeno-associated virus terminal repeated sequences.

18. The method of claim 16 in which the recombinant adeno-associated virus vector lacks adeno-associated virus gene-encoding sequences.

19. The method of claim 16 in which the recombinant adeno-associated virus vector lacks the adeno-associated virus rep gene.

20. The method of claim 16 in which the recombinant adeno-associated virus vector comprises a transcriptional promoter not present in wild-type adeno-associated virus.

21. The method of claim 16 in which the recombinant adeno-associated virus vector is plasmid pAAV/neo, deposited with the ATCC and assigned accession number 68065.

22. The method of claim 16 in which the recombinant helper adeno-associated virus DNA encodes an adeno-associated virus gene located between nucleotide 195 and nucleotide 4480 of the adeno-associated virus genome.

23. The method of claim 16 in which the recombinant helper adeno-associated virus DNA is plasmid AAV-/Ad, deposited with the ATCC and with the accession number 68066.

24. A method for producing a helper-free stock of recombinant adeno-associated virus comprising:
   a) cotransfecting cells permissive for adeno-associated virus replication, in the presence of helper virus infection, with i) a recombinant adeno-associated virus vector which comprises a portion of foreign DNA sequence flanked by adeno-associated virus terminal repeat sequences; and ii) a recombinant helper adeno-associated virus DNA which lacks adeno-associated virus terminal repeat DNA sequences but which comprises adeno-associated virus genes, the expression of which is controlled by adenovirus terminal DNA sequence, such that the helper adeno-associated virus DNA shares no adeno-associated virus sequences with the vector and cannot itself be incorporated into an infectious virion, but provides viral functions sufficient for the replication and packaging into infectious virions of the vector; and
   b) collecting virions so produced.

25. The method of claim 24 in which the adenovirus terminal DNA sequence comprises about the 107 terminal base pairs of the adenovirus genome.

26. The method of claim 24 or 25 in which the recombinant adeno-associated virus vector lacks adeno-associated virus gene-encoding sequences.

27. A method of producing a helper-free stock of recombinant adeno-associated virus comprising:
   a) transfecting, in the presence of a helper virus, a recombinant adeno-associated virus vector which comprises a portion of foreign DNA sequence flanked by a adeno-associated virus terminal repeat DNA sequences into a cell line able to express trans-acting adeno-associated virus functions, which contains a recombinant helper adeno-associated virus DNA which lacks adeno-associated virus terminal repeat sequences but which comprises adeno-associated virus genes, the expression of which is controlled by an element not present in adeno-associated virus, provided that the recombinant adeno-associated virus vector shares no adeno-associated virus sequences with the recombinant helper adeno-associated virus DNA comprised in the cell line; and
   b) collecting virions produced.

28. A method of producing a helper-free stock of recombinant adeno-associated virus comprising:
   a) transfecting, in the presence of a helper virus, a recombinant adeno-associated virus vector which comprises a portion of foreign DNA sequence flanked by a adeno-associated virus terminal repeat DNA sequences into a cell line able to express trans-acting adeno-associated virus functions which contains a recombinant helper adeno-associated virus DNA which lacks adeno-associated virus terminal repeat sequences but which comprises adeno-associated virus genes, the expression of which is controlled by an element not present in adeno-associated virus and in which the element that controls expression of adeno-associated virus genes is adenovirus terminal sequences, provided that the recombinant adeno-associated virus vector shares no adeno-associated virus sequences with the recombinant helper adeno-associated virus DNA comprised in the cell line; and
   b) collecting virions produced.

29. A method of producing a helper-free stock of recombinant adeno-associated virus comprising:
   a) transfecting, in the presence of a helper virus, a recombinant adeno-associated virus vector which comprises a portion of foreign DNA sequence flanked by a adeno-associated virus terminal repeat DNA sequences into a cell line able to express trans-acting adeno-associated virus functions which contains a recombinant helper adeno-associated virus DNA which lacks adeno-associated virus terminal repeat sequences but which comprises adeno-associated virus genes, the expression of which is controlled by an element not present in adeno-associated virus and in which the element that controls expression of adeno-associated virus genes is about the 107 terminal base pairs of the adenovirus genome, provided that the recombinant adeno-associated virus vector shares no adeno-associated virus sequences with the recombinant helper adeno-associated virus DNA comprised in the cell line; and b) collecting virions produced.

30. A recombinant vector which may be used in a process of producing helper-free stocks of recombinant adeno-associated virus, wherein said vector i) is capable of replication in microorganisms, ii) comprises a part of the adeno-associated virus genome capable of providing vital function necessary for replication of a recombinant adeno-associated virus vector and the packaging of the vector into infectious virions; iii) cannot itself be assembled into viral particles to a measurable degree; iv) lacks adeno-associated virus terminal repeat sequence; and v) comprises adenovirus terminal DNA sequence.

31. The vector of claim 30 which is plasmid pAAV-/Ad, deposited with the ATCC and assigned accession number 68066.

32. A recombinant helper adeno-associated virus DNA which lacks adeno-associated virus terminal repeat sequences but which comprises adeno-associated virus genes, the expression of which is under the control of adenovirus terminal sequences.

33. A recombinant helper adeno-associated virus DNA which lacks adeno-associated virus terminal repeat sequences but which comprises adeno-associated virus genes, the expression of which is under the control of about the 107 terminal base pairs of the adenovirus genome.

34. A host cell cotransformant which produces a helper-free stock of recombinant adeno-associated virus and is produced by a method comprising: cotransfecting cells permissive for adeno-associated virus replication, in the presence of helper virus infection with i) a recombinant adeno-associated virus vector which contains a portion of foreign DNA sequence and which can be incorporated into an infectious virion and ii) a recombinant helper adeno-associated virus DNA which (a) provides viral functions sufficient for the replication and packaging into infectious virions of said recombinant adeno-associated virus vector, (b) comprises a nucleotide sequence not found in wild-type adeno-associated virus, that promotes expression of adeno-associated virus genes which results in the provision of viral functions, (c) lacks the adeno-associated virus terminal repeat DNA sequence, (d) shares no adeno-associated virus DNA sequences with said vector, and (e) cannot itself be incorporated into an infectious virion in said cotransfected cells.

35. The host cell cotransformant of claim 34 in which the helper virus is selected from the group consisting of herpesvirus, cytomegalovirus, Epstein-Barr virus, and vaccinia virus.

36. A host cell cotransformant which produces a helper-free stock of recombinant adeno-associated virus and is produced by a method comprising: cotransfecting cells permissive for adeno-associated virus replication, in the presence of helper virus infection with i) a recombinant adeno-associated virus vector which contains a portion of foreign DNA sequence and which can be incorporated into an infectious virion and ii) a recombinant helper adeno-associated virus DNA which (a) provides vital functions sufficient for the replication and packaging into infectious virions of said recombinant adeno-associated virus vector, (b) comprises adenovirus terminal DNA sequence, (c) lacks adeno-associated virus terminal repeat DNA sequence, (d) shares no adeno-associated virus sequences with said vector, and (e) cannot itself be incorporated into an infectious virion in said cotransfected cells.

37. The host cell cotransformant of claim 35 or 36 in which the recombinant adeno-associated virus vector comprises up to about 195 base-pairs of the adeno-associated virus terminal repeated sequences.

38. The host cell cotransformant of claim 35 or 36 in which the recombinant adeno-associated virus vector lacks adeno-associated virus gene-encoding sequences.

39. The host cell cotransformant of claim 35 or 36 in which the recombinant adeno-associated virus vector lacks the adeno-associated virus rep gene.

40. The host cell cotransformant of claim 35 or 36 in which the recombinant adeno-associated virus vector is plasmid pAAV/neo, deposited with the ATCC and assigned accession number 68065.

41. The host cell cotransformant of claim 35 or 36 in which the recombinant helper adeno-associated virus DNA encodes an adeno-associated virus gene located between nucleotide 195 and nucleotide 4480 of the adeno-associated virus genome.

42. The host cell cotransformant of claim 35 or 36 in which the recombinant helper adeno-associated virus DNA is plasmid pAAV/Ad, deposited with the ATCC and with the accession number 68066.

43. The host cell cotransformant of claim 36 in which the helper virus is selected from the group consisting of herpesvirus, cytomegalovirus, Epstein-Barr virus, and vaccinia virus.

44. A host cell cotransformant which produces helper-free stocks of recombinant adeno-associated viruses and is produced by a method comprising: cotransfecting cells permissive for adeno-associated virus replication in the presence of helper virus infection, with i) a recombinant adeno-associated virus vector which comprises a portion of foreign DNA sequence flanked by adeno-associated virus terminal repeat sequences; and ii) a recombinant helper adeno-associated virus DNA which lacks adeno-associated virus terminal repeat DNA sequences but which comprises adeno-associated virus genes, the expression of which is controlled by adenovirus terminal DNA sequence, such that the helper adeno-associated virus DNA shares no adeno-associated virus sequences with the vector and cannot itself be incorporated into an infectious virion, but provides adeno-associated virus functions sufficient for the replication and packaging into infectious virions of the vector.

45. The host cell cotransformant of claim 44 in which the adenovirus terminal DNA sequence comprises about the 107 terminal base pairs of the adenovirus genome.

46. The host cell cotransformant of claim 44 in which the recombinant adeno-associated virus vector lacks adeno-associated virus gene-encoding sequences.

47. The host cell cotransformant of claim 44 in which the recombinant adeno-associated virus vector comprises up to about 195 base pairs of the adeno-associated virus terminal repeated sequences.

* * * * *